US010550184B2

(12) United States Patent
Tekabe et al.

(10) Patent No.: US 10,550,184 B2
(45) Date of Patent: Feb. 4, 2020

(54) HUMANIZED ANTI-RAGE ANTIBODY

(71) Applicant: The Trustees of Columbia University in the City of New York, New York, NY (US)

(72) Inventors: Yared Tekabe, New York, NY (US); Lynne Johnson, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 16/093,106

(22) PCT Filed: Apr. 11, 2017

(86) PCT No.: PCT/US2017/026902
§ 371 (c)(1),
(2) Date: Oct. 11, 2018

(87) PCT Pub. No.: WO2017/180555
PCT Pub. Date: Oct. 19, 2017

(65) Prior Publication Data
US 2019/0119378 A1    Apr. 25, 2019

Related U.S. Application Data

(60) Provisional application No. 62/321,118, filed on Apr. 11, 2016.

(51) Int. Cl.
*C07K 16/28* (2006.01)
*C12N 15/85* (2006.01)
*G01N 33/563* (2006.01)
*G01N 33/577* (2006.01)

(52) U.S. Cl.
CPC .......... *C07K 16/2803* (2013.01); *C12N 15/85* (2013.01); *G01N 33/563* (2013.01); *G01N 33/577* (2013.01); *C07K 2317/54* (2013.01); *C07K 2317/92* (2013.01); *C12N 2015/8518* (2013.01)

(58) Field of Classification Search
CPC ............ C07K 2317/92; C07K 16/2803; C07K 2317/54; G01N 33/563; G01N 33/577; C12N 15/85; C12N 2015/8518
See application file for complete search history.

(56) References Cited

U.S. PATENT DOCUMENTS

| 8,846,397 B2 | 9/2014 | Apostolou et al. |
| 2011/0311448 A1 | 12/2011 | Schmidt et al. |
| 2013/0058936 A1 | 3/2013 | Bruenker et al. |
| 2013/0165389 A1 | 6/2013 | Schellenberger et al. |
| 2014/0242080 A1 | 8/2014 | Jaeger et al. |

FOREIGN PATENT DOCUMENTS

| WO | WO 2010/019656 A1 | 2/2010 |
| WO | WO 2013/026832 A1 | 2/2013 |
| WO | WO 2013/072406 A1 | 5/2013 |
| WO | WO 2013/072415 A1 | 5/2013 |

OTHER PUBLICATIONS

International Search Report dated Jul. 19, 2017 in connection with PCT International Application No. PCT/US2017/026902.
Written Opinion of the International Searching Authority dated Jul. 19, 2017 in connection with PCT International Application No. PCT/US2017/026902.

*Primary Examiner* — Gregory S Emch
(74) *Attorney, Agent, or Firm* — John P. White

(57) ABSTRACT

This invention provides a humanized, anti-human receptor for advance glycation end-products (RAGE) monoclonal antibody or a fragment of such antibody which binds human RAGE as well as compositions containing, and uses of, such antibody and fragments.

25 Claims, 7 Drawing Sheets
Specification includes a Sequence Listing.

Figure 3

```
SEQ ID NO: 11  IGHV4-34*09  QVQLQESGPGLVKPSQTLSLTCAVYGGSF-SYYWSWIRQPPGKGLEWIGEIHHSGSTNY
SEQ ID NO: 12  Yared-HC     DVQLQESGPGLVKPSQSLSLNCSVTGSSIRLGYYRPWIRQFPGNKLEWMGRISYDGSNKY IGHV4-34*09  NPSLKSRVTISVDTSKNQFSLKLSSVTAADTAVYYCARX--------------------
               Yared-HC     SPSLENRISITRDTSKNQYFMKLNSVTTEDTAIYKCVRDRGGNPFFASNGQGTLVTVSS SEQ ID NO: 13  Yared-LC     DIQMTQTTSSLSASLGDRVTINCRASQDISNYLNWYQQKPDGTVKLLIYYTSRLHSGVPS
SEQ ID NO: 14  O8           DIQMTQSPSSLSASVGDRVTITCQASQDISNYLNWYQQKPGKAPKLLIFDASNLETGVPS Yared-LC     RFSGSGSGTDYSLTIGNLEQEDIATYFCQQGNTLPWTFGQGTKV
               O8           RFSGSGSGTDFTFTISSLQPEDIATYYCQQYDNLP---------
```

Binding of biotinylated sRAGE to mouse, chimera, and humanized antibody $K_D$= 88.4 nM (mouse), $R^2$=1.0
$K_D$= 38.17 nM (Chimera), $R^2$=1.0
$K_D$= 42.14 nM (Humanized), $R^2$=1.0

4-20% Novex® Tris-Glycine Gels

Yared Full IgG

1. Tube 1
2. Tube 2
3. Tube 3
4. Tube 4

5. Yared F(ab)₂ after gel filtration (99% purity)

2 ul sample was loaded / lane

HUMANIZED ANTI-RAGE ANTIBODY

This application is a § 371 national stage of PCT International Application. No. PCT/US2017/026902, filed Apr. 11, 2017 and claims the benefit of U.S. Provisional Application No. 62/321,118, filed Apr. 11, 2016, the entire contents of which are hereby incorporated herein by reference.

Throughout this application, certain patents and publications are referenced. Full citations for the publications may be found listed at the end of the specification immediately preceding the claims. The disclosures of all referenced patent publications in their entireties are hereby incorporated by reference into this application in order to more fully describe the state of the art to which this invention pertains.

This application incorporates-by-reference nucleotide and/or amino acid sequences which are present in the file named "170411_87899_PCT_Sequence_Listing_DH.txt", which is 17.0 kilobytes in size, and which was created Apr. 10, 2017 in the IBM-PC machine format, having an operating system compatibility with MS-Windows, which is contained in the text file filed Apr. 11, 2017 as part of this application.

BACKGROUND OF THE INVENTION

Overexpression of the receptor for advanced glycation end products (RAGE) is implicated in the development and progression of several chronic diseases including atherosclerosis, ischemia, cancer, Alzheimer's disease and diabetes, among others. Although monoclonal antibodies have been used to target RAGE in various animal models, a "humanized" version of these antibodies has yet to be developed. This technology is a humanized version of a mouse anti-RAGE antibody that maintains comparable levels of RAGE-binding activity. Further research and development is ongoing and may one day lead to new diagnostic and therapeutic tools for many diseases.

The receptor for advanced glycation end products (RAGE) is a member of the immunoglobulin superfamily of cell surface molecules (Buckley et al.). RAGE is a pattern-recognition receptor capable of binding a diverse range of ligands and is expressed at low levels in most normal tissue. (Buckley et al.). RAGE overexpression is implicated in the development and progression of atherosclerosis, ischemia, cancer, Alzheimer's disease, diabetes, and other illnesses, indicating RAGE as a potential therapeutic target. Studies have shown that monoclonal anti-RAGE mouse antibodies are useful diagnostic and imaging tools in both mice and pigs because of increased uptake at related disease sites. (Johnson L L, et al., 2012; Johnson L L, et al., 2014)

SUMMARY OF THE INVENTION

This invention provides a humanized, anti-human receptor for advance glycation end-products (RAGE) monoclonal antibody comprising:
(a) consecutive amino acids constituting a heavy chain of such antibody, the sequence of which is set forth in SEQ ID NO: 7; and
(b) consecutive amino acids constituting a light chain of such antibody, the sequence of which is set forth in SEQ ID NO: 8,
or a fragment of such antibody which binds human RAGE.

This invention further provides a polypeptide comprising consecutive amino acids and capable of functioning as the heavy chain of an antibody, wherein the sequence of such consecutive amino acids is set forth in SEQ ID NO: 7.

This invention still further provides a polypeptide comprising consecutive amino acids and capable of functioning as the light chain of an antibody, wherein the sequence of such consecutive amino acids is set forth in SEQ ID NO: 8.

BRIEF DESCRIPTION OF THE DRAWINGS

FIG. 3. Alignment of the cloned HC and LC variable regions with the human germline VH4-34 and O8 germline sequences, respectively. CDR regions are underlined. Identical residues are marked with asterisks under the residues. Residues indicated by arrows and bold underline are identified by computer modeling to be retained in the humanized antibody. (IGHV4-34=SEQ ID NO: 11; Yared HC=SEQ ID NO:12; Yared LC=SEQ ID NO:13; O8=SEQ ID NO: 14).

DETAILED DESCRIPTION OF THE INVENTION

Figure 1:
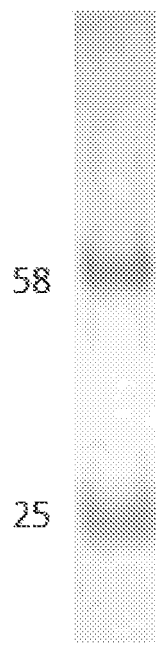
FIG. 1. SDS-PAGE analysis of the purified chimera. 10 mg of purified recombinant mouse-human chimera antibody was resolved by SDS-PAGE, stained with Coomassie Brilliant Blue and destained. The heavy and light chain of the purified anti-RAGE chimeric antibody were clearly present without contaminants.

This invention provides a humanized, anti-human receptor for advance glycation end-products (RAGE) monoclonal antibody comprising:
(a) consecutive amino acids constituting a heavy chain of such antibody, the sequence of which is set forth in SEQ ID NO: 7; and
(b) consecutive amino acids constituting a light chain of such antibody, the sequence of which is set forth in SEQ ID NO: 8, or a fragment of such antibody which binds human RAGE.

Receptor for advanced glycation endproducts (RAGE) is a 35 kDa transmembrane receptor of the immunoglobulin super family. The humanized, anti-human receptor for advance glycation end-products (RAGE) monoclonal antibody of the invention binds human RAGE. The term "humanized" means antibodies from non-human species whose protein sequences have been modified to increase their similarity to antibody variants produced naturally in humans (Reichmann et al.). The protein sequences of antibodies produced in this way are partially distinct from homologous antibodies occurring naturally in humans.

A "fragment of such antibody" comprises the antigen binding portion of the anti-human RAGE antibody described herein. Examples of antibody fragments include, but are not limited to Fv, Fab, Fab', Fab'-SH, F(ab')2; diabodies; linear antibodies; single-chain antibody molecules (e.g., scFv); and multispecific antibodies formed from antibody fragments. Various techniques have been developed for the production of antibody fragments, including proteolytic digestion of antibodies and recombinant production in host cells; however, other techniques for the production of antibody fragments will be apparent to the skilled practitioner. In some embodiments, the antibody fragment of choice is a single chain Fv fragment (scFv). "Single-chain Fv" or "scFv" antibody fragments comprise the V H and V L domains of antibody, wherein these domains are present in a single polypeptide chain. Generally, the Fv polypeptide further comprises a polypeptide linker between the V H and V L domains which enables the scFv to form the desired structure for antigen binding. For a review of scFv and other antibody fragments, see James D. Marks, Antibody Engineering, Chapter 2, Oxford University Press (1995) (Carl K. Borrebaeck, Ed.)

This invention provides a fragment of the humanized, anti-human RAGE antibody of the invention wherein the fragment is a F(ab')2 fragment.

This invention further provides a polypeptide comprising consecutive amino acids and capable of functioning as the heavy chain of an antibody, wherein the sequence of such consecutive amino acids is set forth in SEQ ID NO: 7. This invention still further provides a vector which encodes such a polypeptide. The vector comprises consecutive nucleotides, the sequence of which is set for in SEQ ID NO: 9.

This invention further provides a polypeptide comprising consecutive amino acids and capable of functioning as the light chain of an antibody, wherein the sequence of such consecutive amino acids is set forth in SEQ ID NO: 8. This invention still further provides a vector which encodes such a polypeptide. The vector comprises consecutive nucleotides, the sequence of which is set for in SEQ ID NO: 10.

A "vector" is a replicon, such as plasmid, phage, cosmid, or virus in which another nucleic acid segment may be operably inserted so as to bring about the replication or expression of the segment. The vector may contain one or more additional sequences such as, but not limited to, regulatory sequences (e.g., promoter, enhancer), a selection marker, and a polyadenylation signal. Vectors for transforming a wide variety of host cells are well known to those of skill in the art. They include, but are not limited to, plasmids, phagemids, cosmids, baculoviruses, bacmids, bacterial artificial chromosomes (BACs), yeast artificial chromosomes (YACs), as well as other bacterial, yeast and viral vectors. The vectors described herein may be integrated into the host genome or maintained independently in the cell or nucleus. The terms "express" and "produce" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression/production of an antibody or antigen-binding fragment can be within the cytoplasm of the cell, and/or into the extracellular milieu such as the growth medium of a cell culture.

Recombinant expression vectors contemplated to be within the scope of the description include synthetic, genomic, or cDNA-derived nucleic acid fragments that encode at least one recombinant protein which may be operably linked to suitable regulatory elements. Such regulatory elements may include a transcriptional promoter, sequences encoding suitable mRNA ribosomal binding sites, and sequences that control the termination of transcription and translation. Expression vectors, especially mammalian expression vectors, may also include one or more nontranscribed elements such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a host may also be incorporated. Such vectors may be integrated into the host genome or maintained independently in the cell or nucleus.

The vectors described herein can be used to transform various cells with the genes encoding the disclosed polypeptides. Thus, another aspect features host cells transformed with vectors comprising a nucleic acid sequence encoding a polypeptide. Numerous host cells are known in the art and are considered to be within the scope of this disclosure.

This invention provides a eucaryotic cell which expresses the monoclonal antibody described herein.

This invention still further provides a eucaryotic cell comprising a vector comprising consecutive nucleotides, the sequence of which is set for in SEQ ID NO: 9, and comprising a vector comprising consecutive nucleotides, the sequence of which is set for in SEQ ID NO: 10. In one aspect of the invention, the eucaryotic cell of this invention is a mammalian cell. In one aspect of the invention, the eucaryotic cell is a Chinese hamster ovary (CHO) cell. In one aspect of the invention, the eucaryotic cell is a human cell. In one aspect of the invention, the eucaryotic cell the human cell is a human kidney 293 cell.

Numerous techniques are known in the art for the introduction of foreign genes into cells and may be used to construct the recombinant cells for purposes of carrying out the inventive methods and producing polypeptides as described herein, in accordance with the various embodiments described and exemplified herein. The technique used should provide for the stable transfer of the heterologous gene sequence to the host cell, such that the heterologous gene sequence is heritable and expressible by the cell progeny, and so that the necessary development and physiological functions of the recipient cells are not disrupted. Techniques which may be used include but are not limited to chromosome transfer (e.g., cell fusion, chromosome mediated gene transfer, micro cell mediated gene transfer), physical methods (e.g., transfection, spheroplast fusion, microinjection, electroporation, liposome carrier), viral vector transfer (e.g., recombinant DNA viruses, recombinant RNA viruses) and the like. Calcium phosphate precipitation and polyethylene glycol (PEG)-induced fusion of bacterial protoplasts with mammalian cells can also be used to transform cells.

This invention further provides a process for producing a humanized, anti-human RAGE monoclonal antibody, which comprises culturing a eucaryotic cell comprising a first vector which includes consecutive nucleotides, the sequence of which is set forth in SEQ ID NO: 9, and a second vector which includes consecutive nucleotides, the sequence of which is set forth in SEQ ID NO: 10 under conditions such that the humanized anti-human RAGE monoclonal antibody is expressed and recovering the antibody so expressed. Suitable eukaryotic cells are mammalian cells, for example Chinese hamster ovary (CHO) cells and human cells, for example a human kidney 293 cell.

This invention further provides a composition comprising the humanized antibody or fragment of such antibody of the invention and a pharmaceutically acceptable carrier.

The described antibody or fragment can be administered to said subject in the form of such a composition. Each of the described antibodies or fragments can be included in such a composition. Such compositions can also include other agents, such as preservatives, antimicrobial agents, excipients and the like.

Described herein are compositions comprising at least one disclosed antibody or fragment and a pharmaceutically acceptable carrier. The compositions can be formulated as any of various preparations that are known and suitable in the art, including those described herein. In some embodiments, the compositions are aqueous formulations. Aqueous solutions can be prepared by admixing the antibody or fragment in water or suitable physiologic buffer, and optionally adding suitable colorants, flavors, preservatives, and stabilizing agents.

As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable substances such as wetting or minor amounts of auxiliary substances such as wetting or emulsifying agents, preservatives or buffers, which enhance the shelf life or effectiveness of the antibody or antibody fragment.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody fragment) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies and antibody fragments of the present invention can be administered by a variety of methods known in the art, although for many therapeutic applications, the preferred route/mode of administration is intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

In certain embodiments, an antibody or antibody fragment of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

The subject can be any animal, and preferably is a mammal such as a mouse, rat, hamster, guinea pig, rabbit, cat, dog, monkey, donkey, cow, horse, pig, and the like. In one aspect of the invention, the mammal is a human. In one aspect of the invention, the mammal is other than a human.

This invention still further provides a method for treating a subject suffering from a disorder or condition which comprises administering to the subject an amount of the composition according to claim 20 effective to treat the subject. In one aspect of the invention, the disorder or condition is selected from the group consisting of Amytropic Lateral Sclerosis, Brachial Plexus Injury, Brain Injury, including traumatic brain injury, Cerebral Palsy, Friedrich's Ataxia, Guillain Barre, Leukodystrophies, Multiple Sclerosis, Post Polio, Spina Bifida, Spinal Cord Injury, Spinal Muscle Atrophy, Spinal Tumors, Stroke, Transverse Myelitits, dementia, senile dementia, mild cognitive impairment, Alzheimer-related dementia, Huntington's chorea, tardive dyskinesia, hyperkinesias, manias, Morbus Parkinson, steel-Richard syndrome, Down's syndrome, myasthenia gravis, nerve trauma, vascular amyloidosis, cerebral hemorrhage I with amyloidosis, brain inflammation, Friedrich's ataxia, acute confusion disorder, amyotrophic lateral sclerosis, atherosclerosis, glaucoma, Alzheimer's disease, diabetic nephropathy, sepsis, rheumatoid arthritis and related inflammatory diseases, inflammation, ischemia, cancer, thrombocytopenia, chemotherapy-induced thrombocytopenia, stem cell transplant-induced thrombocytopenia, diabetes, diabetic kidney disease, diabetic macrovascular disease, diabetic nephropathy, diabetic neuropathy, diabetic retinopathy, and diabetic heart failure.

This invention further provides a detectably labeled antibody comprising the humanized antibody or fragment of the invention, and a detectable label attached to such antibody or fragment.

As used herein, "detectable label" refers to a molecule capable of detection using methods known in the art including radiography, fluorescence, chemiluminescence, enzymatic activity, absorbance, and the like. Detectable labels include radioisotopes, fluorophores, chromophores, enzymes, dyes, metal ions, ligands such as biotin, avidin, strepavidin and haptens, quantum dots, and the like.

This invention further a method for detecting human RAGE in human tissue comprising contacting the tissue with the labeled antibody or fragment of the invention under conditions permitting the antibody or fragment to bind to human RAGE present in the tissue, and detecting the labeled antibody or fragment bound to the tissue, so as to detect the presence of human RAGE in the tissue.

This invention further provides method for producing an image of human RAGE in a human tissue which comprises contacting the human tissue with the labeled antibody or fragment of the invention under conditions permitting the labeled antibody or fragment to bind to human RAGE present in the tissue, wherein the labeled antibody or fragment is imageable, and producing the image of human RAGE in the tissue using the imageable labeled antibody or fragment.

As used herein "imageable" means capable of being imaged.

Reference to Other Publications or References and to the Experimental Details

The present invention is not intended to be limited by any theory. This invention will be better understood by reference to the Experimental Details which follow, but those skilled in the art will readily appreciate that the specific experiments detailed are only illustrative of the invention as defined in the claims which follow thereafter.

EXPERIMENTAL DETAILS

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only.

Example 1—Molecular Cloning of an Anti-RAGE Antibody and Humanization of the Cloned Antibody 1. Cloning of the Variable Region of the Light and Heavy Change of an Anti-RAGE from Frozen Hybridoma Cells.

From frozen hybridoma cells expressing the anti-RAGE monoclonal antibody (mAb) (IgG2a isotype with a Kappa light chain), total RNA was prepared from the cell pellet and cDNA was generated by RT-PCR. The cDNA was then used as templates for PCR amplification of the antibody light and heavy chain variable regions.

a. Cloning of Antibody Variable Regions.

A reverse primer based on the mouse kappa light constant region was used for 5'-RACE PCR to amplify the light chain variable region. A reverse primer based on the mouse IgG2a heavy chain constant region was used for 5'-RACE PCR to amplify the heavy chain variable region. The amplified PCR products were cloned into a TOPO vector for sequencing analysis.

b. Sequencing Analysis of the Cloned Variable Regions.

10 clones for each variable region were sequenced. All of the 10 heavy chain clones showed an identical coding region for the heavy chain, and all of the 10 light chain clones showed an identical coding region for the light chain, suggesting that the identified heavy and light chain variable sequences are likely to be the bona fide genes coding for the anti-RAGE antibody. The variable sequences of the heavy and light chain genes are shown below:

Heavy chain nucleotide sequence (SEQ ID NO: 1):
ATGAAAGTGTTGAGTCTGTTGTACCTGTTGACAGCCATTCCTGGTATCCT

GTCTGATGTACAGCTTCAGGAGTCAGGACCTGGCCTCGTGAAACCTTCTC

AGTCTCTGTCTCTCAACTGCTCTGTCACTGGCTCCTCCATCACCAGTGGT

TATTACTGGAACTGGATCCGGCAGTTTCCAGGAAACAAACTGGAATGGAT

GGGCGACATAAGCTACGATGGTAGCAATAACTACAACCCATCTCTCAAAA

ATCGAATCTCCATCACTCGTGACACATCTAAGAACCAGGTTTTCATGAAG

TTGAATTCTGTGACTACTGAGGACACAGCCATATATAAATGTGTAAGAGA

AGACAGGTCGGGCTACCCCCCGTTTGCTAACTGGGGCCAAGGGACTCTGG

TCACTGTCTCTGCA

Heavy chain amino acid sequence (SEQ ID NO: 2):
MKVLSLLYLLTAIPGILSDVQLQESGPGLVKPSQSLSLNCSVTGSSITSG

YYWNWIRQFPGNKLEWMGDISYDGSNNYNPSLKNRISITRDTSKNQVFMK

LNSVTTEDTAIYKCVREDRSGYPPFANWGQGTLVTVSA

Light chain nucleotide sequence (SEQ ID NO: 3):
ATGATGTCCTCTGCTCAGTTCCTTGGTCTCCTGTTGCTCTGTTTTCAAGG

TACCAGATGTGATGTCCAGATGACACAGACTACATCCTCTTTGTCTGCCT

CTCTGGGAGACAGAGTCACCATCAATTGCAGGGCAAGTCAGGACATTAGC

AATTATTTALACTGGTATCAGCAGAAACCAGATGGAACTGTTAAACTCCT

GATCTACTACACATCAAGATTACACTCAGGAGTCCCATCAAGGTTCAGTG

GCAGTGGGTCTGGAACAGATTATTCTCTCACCATTAGCAACCTGGAGCAA

GAAGATATTGCCACTTACTTTTGCCAACAGGGTAATACGCTTCCGTGGAC

GTTCGGTGGAGGCACGAAGCTGGAAATCAAA

Light chain amino acid sequence (SEQ ID NO: 4):
MSSAQFLGLLLLCFQGTRCDVQMTQTTSSLSASLGDRVTINCRASQDISN

YLNWYQQKPDGTVKLLIYYTSRLHSGVPSRFSGSGSGTDYSLTISNLEED

IATYFCQQGNTLPWTFGGGTKLEIK

2. Cloning of the Variable Regions of the Light and Heavy Chain Variable Regions into Mammalian Expression Vectors and In Vitro Antibody Production The light chain variable region was PCR amplified from the light chain TOPO clone and cloned into the Afl II and Acc65 I sites of a pcDNA3.4-kappa vector and sequencing confirmed.

The entire light chain sequence of the mouse-human chimera is shown below (SEQ ID NO: 5):

METGLRWLLLVAVLKGVQCDIQMTQTTSSLSASLGDRVTINCRASQDISN

YLNWYQQKPDGTVKLLIYYTSRLHSGVPSRFSGSGSGTDYSLTISNLEQE

DIATYFCQQGNTLPWTFGQGTKVEIKRTVAAPSVFIFPPSDEQLKSGTAS

VVCLLNNFYPREAKVQWKVDNALQSGNSQESVTEQDSKDSTYSLSSTLTL

SKADYEKHKVYACEVTHQGLSSPVTKSFNRGEC

Similarly, the heavy chain variable region was PCR amplified from the corresponding heavy chain TOPO clone, and cloned into BamH I and Apa I sites of a pcDNA3.4-IgG1 vector and sequencing confirmed.

The entire heavy chain sequence of the mouse-human chimera is shown below (SEQ ID NO: 6):

MDTRAPTQLLGLLLLWLPGSRCDVQLQESGPGLVKPSQSLSLNCSVTGSS

ITSGYYWNWIRQFPGNKLEWMGDISYDGSNNYNPSLKNRISITRDTSKNQ

VFMKLNSVTTEDTAIYKCVREDRSGYPPFANWGQGTLVTVSSASTKGPSV

FPLAPSSKSTSGGTAALGCLVKDYFPEPVTVSWNSGALTSGVHTFPAVLQ

SSGLYSLSSVVTVPSSSLGTQTYICNVNHKPSNTKVDKRVEPKSCDKTHT

CPPCPAPEFEGGPSVFLFPPKPKDTLMISRTPEVTCVVVDVSHEDPEVKF

NWYVDGVEVHNAKTKPREEQYNSTYRVVSVLTVLHQDWLNGKAYACAVSN

KALPAPIEKTISKAKGQPREPQVYTLPPSRDELTKNQVSLTCLVKGFYPS

DIAVEWESNGQPENNYKTTPPVLDSDGSFFLYSKLTVDKSRWQQGNVFSC

SVMHEALHNHYTQKSLSLSPGK

Large scale plasmid preparations were prepared and used for transfection of human kidney 293 cells. Secreted antibody was purified from the culture medium 5 days post transfection using Protein A affinity chromatography. Purified antibody was analyzed by SDS-PAGE gel to determine the purity of the antibody, which is estimated to be greater than 95% pure (FIG. 1). The antibody concentration was determined with Lowry protein assay.

3. Affinity Determination of the Purified Chimera and Original Mouse Antibody.

Figure 2:
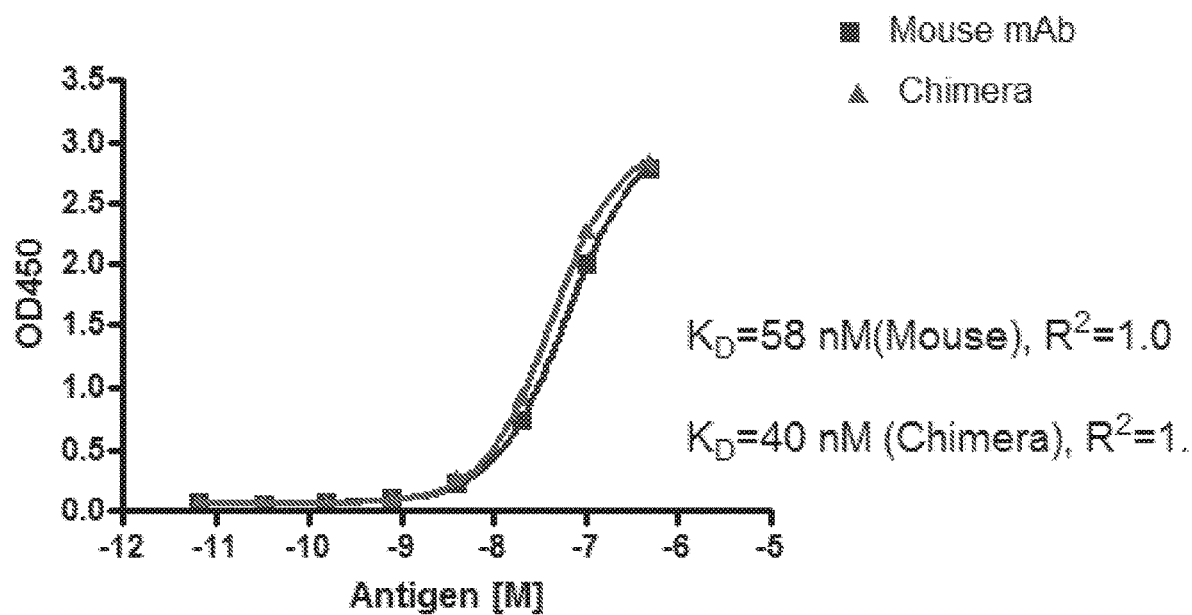
FIG. 2. Affinity determination for the mouse and chimera antibodies. Duplicates of the diluted antigens were added to antibody-coated wells. Bound antigen was detected with HRPstreptavidin and TMB substrate. The OD450 readings were analyzed with GraphPad Prism software using non-linear regression fit. R2 for both curves were 1.0, indicating perfect fits.

250 ng of the purified chimeric antibody or the original murine antibody were coated in the wells of a 96 well ELISA plate overnight. The sRAGE antigen was labeled with biotin to a final biotin density of 2.3 biotins/protein molecule. Serial dilution of the labeled antigen was then added to the antibody-coated wells. Captured antigen was detected with HRP-conjugated streptavidin. FIG. 2 shows the antigen binding curves of the mouse and chimeric antibody for sRAGE. Curve-fit analysis using Prism software indicated that the affinity of the mouse antibody for sRAGE was 58 nM, and the affinity of the chimera for the antigen was 40 nM, suggesting that the cloned antibody genes are correct and express the anti-RAGE variable regions.

0.5 mg of the purified chimera antibody were tested. Testing confirmed the activity of the cloned chimeric antibody. Applicants therefore continued with the humanization of this cloned antibody.

4. Humanization of the Cloned Antibody.

Alignments of the cloned murine heavy chain (HC) and light chain (LC) variable regions with human germline antibody variable regions were performed to identify the best frameworks as acceptors for the mouse HC and LC. Based on the alignment analysis, the human VH4-34 was selected for the HC humanization and the O8 light chain was selected for the LC humanization. The aligned sequences are presented in FIG. 3.

Computer modeling and analysis were performed for the mouse antibody and humanized antibody with the selected human antibody frameworks and mouse antibody CDRs. The light chains of the mouse and O8 antibody are almost identical, the differences in the frameworks between the human and mouse antibody are not likely to impact the shape of LC CDRs, therefore, no mouse residue was considered necessary to be introduced to the LC framework to restore activity of the grafted humanized LC.

The VH4-34 has one less amino compared to the murine anti-RAGE HC immediately preceding CDRH1. This deletion in the CDR grafted VH4-34 framework compared to the murine mAb will change the shape of CDRH1 and will alter the shape of the antigen-binding pocket directly and influence the CDRH3 conformation. Therefore, modeling indicated that the two residues preceding CDRH1 indicated with arrows and by bold letters (FIG. 3) should be included in the humanized antibody to retain activity in the grafted humanized sequence.

Residue 71 in the murine anti-RAGE antibody HC was predicted by the modeling to be important for maintaining the conformation of CDRH2, therefore, the murine residue R71 was kept.

Based on the antibody modeling, the sequences of the humanized antibody HC and LC are designed and presented below.

Amino Acid Sequences of the Humanized HC and LC.

Underlined residues are taken from the murine antibody. Non-underlined residues in are from the human germline.

Heavy chain (SEQ ID NO: 7):
QVQLQESGPGLVKPSQTLSLTCAVYGGSITSGYYWNWIRQPPGKGLEWIG
DISYDGSNNYNPSLKSRVTISRDTSKNQFSLKLSSVTAADTAVYYCVRED
RSGYPPFANWGQGTLVTVSS Light chain (SEQ ID NO: 8):
DIQMTQSPSSLSASVGDRVTITCQASQDISNYLNWYQQKPGKAPKLLIYY
TSRLHSGVPSRFSGSGSGTDFTFTISSLQPEDIATYYCQQGNTLPWTFGQ
GTKV DNA fragments encoding the humanized amino acids shown below were synthesized and cloned into antibody expression vectors.

Nucleotide Sequences of Humanized HC and LC.

Synthesized HC (SEQ ID NO: 9):
GGATCCAGATGCCAGGTGCAGCTGCAGGAAAGCGGCCCTGGCCTGGTGAA

ACCCAGCCAGACCCTGAGCCTGACCTGCGCCGTGTACGGCGGCAGCATCA

CCAGCGGCTACTACTGGAACTGGATCAGACAGCCCCCTGGCAAGGGCCTG

GAATGGATCGGCGACATCAGCTACGACGGCAGCAACAACTACAACCCCAG

CCTGAAGTCCAGAGTGACCATCAGCCGGGACACCAGCAAGAACCAGTTCA

-continued

GCCTGAAGCTGAGCAGCGTGACAGCCGCCGACACCGCCGTGTACTACTGC

GTGCGCGAGGACAGAAGCGGCTACCCCCCCTTCGCCAATTGGGGCCAGGG

CACCCTGGTGACAGTGTCCAGCGCCAGCACCAAGGGCCCC

Synthesized LC (SEQ ID NO: 10):
CTTAAGGGCGTGCAGTGCGACATCCAGATGACCCAGAGCCCCAGCAGCCT

GAGCGCCAGCGTGGGCGACAGAGTGACCATCACCTGTCAGGCCAGCCAGG

ACATCAGCAACTACCTGAACTGGTATCAGCAGAAGCCCGGCAAGGCCCCC

AAGCTGCTGATCTACTACACCTCCCGGCTGCACAGCGGCGTGCCCAGCAG

ATTTTCTGGCAGCGGCAGCGGCACCGACTTCACCTTCACCATCAGCAGCC

TGCAGCCCGAGGATATCGCCACCTACTACTGCCAGCAGGGCAACACCCTG

CCCTGGACCTTCGGCCAGGGTACC

Figure 4:
FIG. 4. SDS-PAGE analysis of the purified humanized antibody. 10 mg of purified humanized antibody was resolved by SDS-PAGE, stained with Coomassie Brilliant Blue and de-stained.

Large scale plasmid preparations were made and used for transfection as described above. The purified antibody is estimated to be greater than 95% pure (FIG. 4).

5. Affinity Determination of the Purified Humanized, Chimera, and Original Murine Monoclonal Anti-RAGE Antibody.

Figure 5:
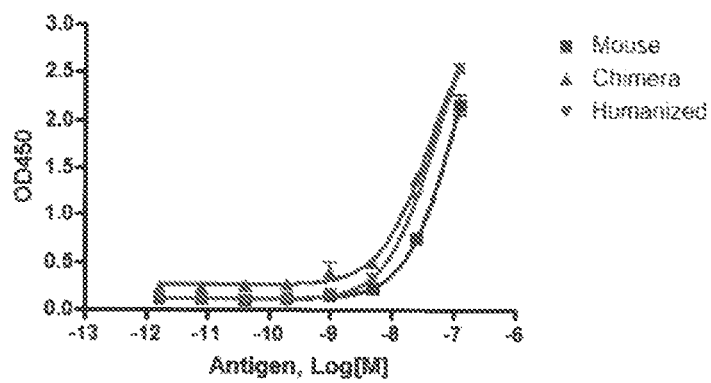
FIG. 5. Affinity determination for the humanized, chimeric and murine antibodies. Duplicates of the diluted antigens were added to antibody-coated wells. Bound antigen was detected with HRP-streptavidin and TMB substrate. The OD450 readings were analyzed with GraphPad Prism software using non-linear regression fit. The R2 values for all 3 curves were 1.0, indicating perfect fits of these curves.

Affinity determination was performed for the humanized, chimeric and the original murine anti-RAGE antibody as described above. The affinity of the murine antibody for RAGE was determined to be 88.4 nM, the affinity of the chimera for the RAGE antigen was 38.7 nM, and the affinity for the humanized antibody for the RAGE antigen was 42.14 nM (FIG. 5), which is almost identical to that of the chimeric antibody, and is within the 3 fold shift described in proposal.

0.5 mg of the purified humanized antibody was then tested.

Conclusion

Based on the data presented above, we conclude that we have cloned the HC and LC variable regions of the mouse anti-RAGE antibody from the original frozen hybridoma cells and have successfully humanized the antibody while retaining its binding activity within 2-fold of that of the chimeric anti-RAGE antibody.

Example 2—Large Scale Production of Full-Length IgG and F(ab)2' of a Humanized Anti-RAGE Antibody 1. Introduction From frozen hybridoma cells expressing the anti-RAGE monoclonal antibody (mAb) (IgG2a isotype with a Kappa light chain) total RNA was prepared from the cell pellet and cDNA was generated by RT-PCR. The cDNA was then used as templates for PCR amplification of the light and heavy chain variable regions. The cloned antibody genes were expressed as a mouse-human chimera. This cloned antibody was then humanized.

The affinity of the mouse antibody for RAGE was determined by ELISA to be 62.6 nM, the affinity of the chimera for the antigen was 103.6 nM, and the affinity for the humanized antibody was 133.4 nM for biotinylated sRAGE.

The goal of this final stage of the project is generate 100 mg of full length IgG1 of the humanized antibody and 10 mg of F(ab')2.

2. Methods a. Full-Length IgG Production 293F cells were transfected with pCDNA3.4-HC and pCDNA3.4-LC. 5-6 days post transfection, culture media were collected and antibody purified using protein A column (MabSelect SuRe, GE), eluted with 0.1M glycine pH 3 and neutralized using 1M Tris pH 8. The eluted antibody was subjected to dialysis with 1×PBS. Protein concentrations were determined using A280 absorbance with the appropriate IgG extinction coefficient.

b. F(ab')2 Preparation 60 mg of full-length IgG were digested with 1.5 ml of immobilized Pepsin (ThermoScientific). The digestion reaction was incubated at 370 C for 2.5 hours. The solution was then centrifuged at 1,000 g for 3 minutes to separate the digest solution from the immobilized Pepsin. Samples were analyzed by SDS-PAGE (reduced and non-reduced) FIG. 1, and subjected to dialysis using a 10 kDa cutoff dialysis tube with 1×PBS. Protein concentration was determined using A280).

Another 60 mg of full-length IgG were digested similarly. The solution was then centrifuged at 1,000 g for 3 minutes to separate the digest solution from the immobilized Pepsin. Samples were further purified with SEC column and the fractions for F(ab')2 were pooled, concentrated, and dialyzed with 1×PBS.

c. Affinity Determination of Purified IgG1 and F(ab')2

250 ng of the purified IgG1 or F(ab')2 antibody were coated in the wells of a 96 well ELISA plate overnight. The sRAGE antigen was labeled with biotin to a final density of 4.2 biotin/protein. Serial dilution of the labeled antigen was then added to the antibody-coated wells. Captured antigen was detected with HRP-conjugated streptavidin. Data were analyzed with Graphpad Prism software.

Results

Figure 6:
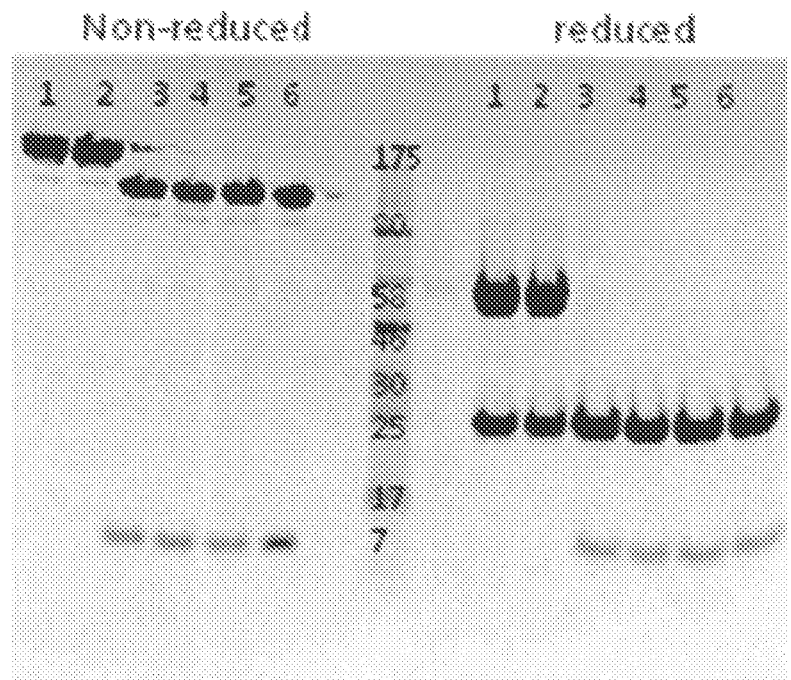
FIG. 6. SDS-PAGE gel using reduced and non-reduced conditions. Samples of the digestion reaction input, after incubation, and after dialysis were analyzed with SDS-PAGE gel using reduced and non-reduced conditions.
Figure 7:
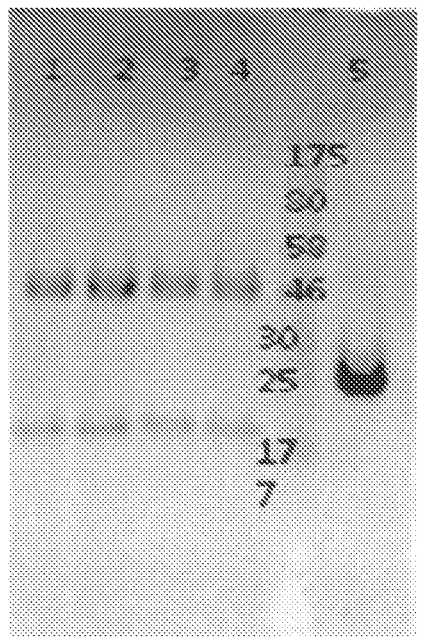
FIG. 7. SDS-PAGE gel of purified full length IgG antibody from 4 tubes and SEC purified F(ab')2.
Figure 8:
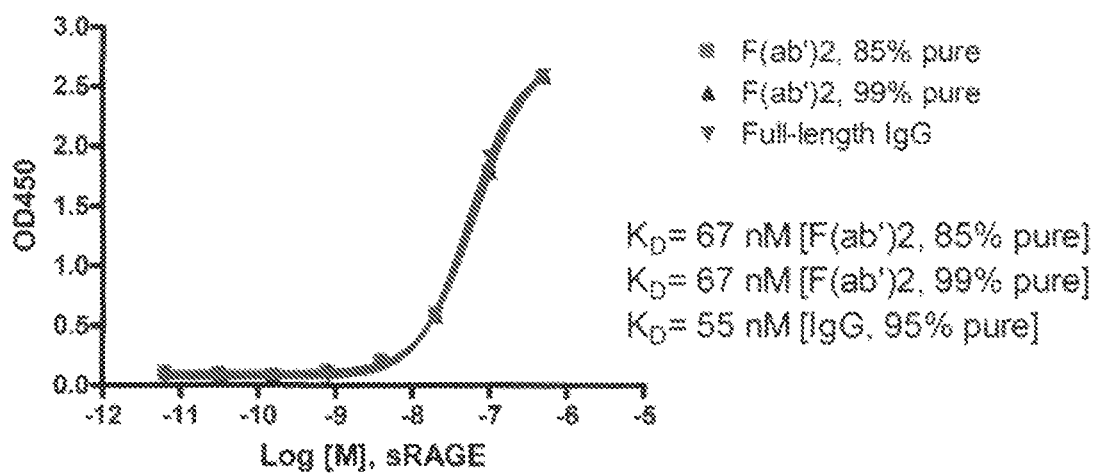
FIG. 8. Affinity determination for the purified IgG and F(ab')2 antibodies. Duplicates of the diluted antigens were added to antibody coated wells. Bound antigen was detected with HRP-streptavidin and TMB substrate. The OD450 readings were analyzed with GraphPad Prism software using non-linear regression fit. R2 for all 3 curves were 1.0, indicating perfect fits of these curves.

F(ab')2 after digestion was 80-85% pure with an additional 7 kDa fragment that corresponds to a small Fc fragment that cannot be removed with protein A resins or dialysis (FIG. 6). An aliquot of the digested antibodies was further purified with gel filtration chromatography to remove the 7 kDa fragment. The SEC step increased the purity to ~99% (FIG. 7). The affinity data presented in FIG. 8 indicates that both the purified full-length IgG and the 2 batches of F(ab')2 retained full antibody binding affinity between 55-66 nM similar to previously observed affinity for mouse antibody, but higher than that of the humanized antibody observed in the previous experiment. The reason could be due to the quality of the antigen, since different batches of antigens were used.

Conclusions

Based on the data presented above, both purified full-length IgG and F(ab')2 retained full activity. A total of 100 mg of full-length IgG and 30 mg of F(ab')2 at 85% purity and 9.0 mg of F(ab')2 at 99% purity were generated.

REFERENCES

Buckley, Stephen T. et al. "The Receptor for Advanced Glycation End Products (RAGE) and the Lung," *J Biomed and Biotech*, vol. 2010, Article ID 917108, 11 pages, 2010.

Cole et al., in *Monoclonal Antibodies and Cancer Therapy*, Alan R. Liss, Inc. 77-96 (1985)

Johnson L L, et al., "Imaging of receptors for advanced glycation end products in experimental myocardial ischemia and reperfusion injury," *JACC Cardiovasc Imaging*, vol. 5, issue 1, pgs 56-67, 2012.

Johnson L L, et al., "Imaging RAGE expression in atherosclerotic plaques in hyperlipidemic pigs," *EJNMMI Res*, vol. 4, issue 26, 2014.

Jones et al., *Nature* 331:522-25 (1986).
Kozbor et al., *Immunol. Today* 4:72 (1983)
Marks, James D., *Antibody Engineering*, Chapter 2, Oxford University Press (1995) (Carl K. Borrebaeck, Ed.)
Presta, *Curro Opin. Struct. Biol.* 2:593-96 (1992).
Riechmann et al., *Nature* 332:323-27 (1988).
Robinson, J. R., ed. Sustained and Controlled Release Drug Delivery Systems, Marcel Dekker, Inc., New York, 1978.

What is claimed is:

1. A humanized, anti-human receptor for advance glycation end-products (RAGE) monoclonal antibody comprising:
    (a) consecutive amino acids constituting a heavy chain of such antibody, the sequence of which is set forth in SEQ ID NO: 7; and
    (b) consecutive amino acids constituting a light chain of such antibody, the sequence of which is set forth in SEQ ID NO: 8,
    or a fragment of such antibody which binds human RAGE.

2. The fragment of the humanized, anti-human RAGE antibody of claim 1 wherein the fragment is a F(ab')2 fragment.

3. A polypeptide comprising consecutive amino acids and capable of functioning as the heavy chain of an antibody, wherein the sequence of such consecutive amino acids is set forth in SEQ ID NO: 7.

4. A polypeptide comprising consecutive amino acids and capable of functioning as the light chain of an antibody, wherein the sequence of such consecutive amino acids is set forth in SEQ ID NO: 8.

5. A vector which encodes the polypeptide of claim 3.

6. The vector of claim 5, comprising consecutive nucleotides, the sequence of which is set for in SEQ ID NO: 9.

7. A vector which encodes the polypeptide of claim 4.

8. The vector of claim 7, comprising consecutive nucleotides, the sequence of which is set for in SEQ ID NO: 10.

9. A eukyotic cell which expresses the monoclonal antibody of claim 1.

10. The eukaryotic cell of claim 9 comprising a vector comprising consecutive nucleotides, the sequence of which is set forth in SEQ ID NO: 9, and comprising a vector comprising consecutive nucleotides, the sequence of which is set forth in SEQ ID NO: 10.

11. The eukaryotic cell of claim 9, wherein the eucaryotic cell is a mammalian cell.

12. The mammalian cell of claim 11, wherein the mammalian cell is a Chinese hamster ovary (CHO) cell.

13. The mammalian cell of claim 11, wherein the mammalian cell is a human cell.

14. The human cell of claim 13, wherein the human cell is a human kidney 293 cell.

15. A process for producing a humanized, anti-human RAGE monoclonal antibody, comprising culturing a eukaryotic cell according to claim 9 under conditions such that the humanized anti-human RAGE monoclonal antibody is expressed and recovering the antibody so expressed.

16. The process of claim 15, wherein the eukaryotic cell is a mammalian cell.

17. The process of claim 16, wherein the mammalian cell is a Chinese hamster ovary (CHO) cell.

18. The process of claim 16, wherein the mammalian cell is a human cell.

19. The process of claim 18, wherein the human cell is a human kidney 293 cell.

20. A composition comprising the humanized antibody or fragment of such antibody of claim 1 and a pharmaceutically acceptable carrier.

21. A method for treating a subject suffering from a disorder or condition associated with RAGE overexpression, which comprises administering to the subject an amount of the composition according to claim 20 effective to treat the subject.

22. The method of claim 21, wherein the disorder or condition is selected from the group consisting of Amytropic Lateral Sclerosis, Brachial Plexus Injury, Brain Injury, including traumatic brain injury, Cerebral Palsy, Friedrich's Ataxia, Guillain Barre, Leukodystrophies, Multiple Sclerosis, Post Polio, Spina Bifida, Spinal Cord Injury, Spinal Muscle Atrophy, Spinal Tumors, Stroke, Transverse Myelitits, dementia, senile dementia, mild cognitive impairment, Huntington's chorea, tardive dyskinesia, hyperkinesias, manias, Morbus Parkinson, steel-Richard syndrome, Down's syndrome, myasthenia gravis, nerve trauma, vascular amyloidosis, cerebral hemorrhage I with amyloidosis, brain inflammation, Friedrich's ataxia, acute confusion disorder, amyotrophic lateral sclerosis, atherosclerosis, glaucoma, Alzheimer's disease, diabetic nephropathy, sepsis, rheumatoid arthritis and related inflammatory diseases, inflammation, ischemia, cancer, thrombocytopenia, chemotherapy-induced thrombocytopenia, stem cell transplant-induced thrombocytopenia, diabetes, diabetic kidney disease, diabetic macrovascular disease, diabetic nephropathy, diabetic neuropathy, diabetic retinopathy, and diabetic heart failure.

23. A detectably labeled antibody comprising the humanized antibody or fragment of claim 1, and a detectable label attached to such antibody or fragment.

24. A method for detecting human RAGE in human tissue comprising contacting the tissue with the labeled antibody or fragment of claim 23 under conditions permitting the antibody or fragment to bind to human RAGE present in the tissue, and detecting the labeled antibody or fragment bound to the tissue, so as to detect the presence of human RAGE in the tissue.

25. A method for producing an image of human RAGE in a human tissue which comprises contacting the human tissue with the labeled antibody or fragment of claim 23 under conditions permitting the labeled antibody or fragment to bind to human RAGE present in the tissue, wherein the labeled antibody or fragment is imageable, and producing the image of human RAGE in the tissue using the imageable labeled antibody or fragment.

* * * * *

SEQUENCE LISTING

<160> NUMBER OF SEQ ID NOS: 14

<210> SEQ ID NO 1
<211> LENGTH: 414
<212> TYPE: DNA
<213> ORGANISM: Mus musculus

<400> SEQUENCE: 1

```
atgaaagtgt tgagtctgtt gtacctgttg acagccattc ctggtatcct gtctgatgta      60
cagcttcagg agtcaggacc tggcctcgtg aaaccttctc agtctctgtc tctcaactgc     120
tctgtcactg gctcctccat caccagtggt tattactgga actggatccg gcagtttcca     180
ggaaacaaac tggaatggat gggcgacata agctacgatg gtagcaataa ctacaaccca     240
tctctcaaaa atcgaatctc catcactcgt gacacatcta agaaccaggt tttcatgaag     300
ttgaattctg tgactactga ggacacagcc atatataaat gtgtaagaga agacaggtcg     360
ggctaccccc cgtttgctaa ctggggccaa gggactctgg tcactgtctc tgca           414
```

<210> SEQ ID NO 2
<211> LENGTH: 138
<212> TYPE: PRT
<213> ORGANISM: Mus musculus

<400> SEQUENCE: 2

```
Met Lys Val Leu Ser Leu Leu Tyr Leu Leu Thr Ala Ile Pro Gly Ile
1               5                   10                  15

Leu Ser Asp Val Gln Leu Gln Glu Ser Gly Pro Gly Leu Val Lys Pro
            20                  25                  30

Ser Gln Ser Leu Ser Leu Asn Cys Ser Val Thr Gly Ser Ser Ile Thr
        35                  40                  45

Ser Gly Tyr Tyr Trp Asn Trp Ile Arg Gln Phe Pro Gly Asn Lys Leu
    50                  55                  60

Glu Trp Met Gly Asp Ile Ser Tyr Asp Gly Ser Asn Asn Tyr Asn Pro
65                  70                  75                  80

Ser Leu Lys Asn Arg Ile Ser Ile Thr Arg Asp Thr Ser Lys Asn Gln
                85                  90                  95

Val Phe Met Lys Leu Asn Ser Val Thr Thr Glu Asp Thr Ala Ile Tyr
            100                 105                 110

Lys Cys Val Arg Glu Asp Arg Ser Gly Tyr Pro Pro Phe Ala Asn Trp
        115                 120                 125

Gly Gln Gly Thr Leu Val Thr Val Ser Ala
    130                 135
```

<210> SEQ ID NO 3
<211> LENGTH: 381
<212> TYPE: DNA
<213> ORGANISM: Mus musculus

<400> SEQUENCE: 3

```
atgatgtcct ctgctcagtt ccttggtctc ctgttgctct gttttcaagg taccagatgt      60
gatgtccaga tgacacagac tacatcctct ttgtctgcct ctctgggaga cagagtcacc     120
atcaattgca gggcaagtca ggacattagc aattatttaa actggtatca gcagaaacca     180
```

```
gatggaactg ttaaactcct gatctactac acatcaagat tacactcagg agtcccatca      240
aggttcagtg gcagtgggtc tggaacagat tattctctca ccattagcaa cctggagcaa      300
gaagatattg ccacttactt ttgccaacag ggtaatacgc ttccgtggac gttcggtgga      360
ggcacgaagc tggaaatcaa a                                                381
```

<210> SEQ ID NO 4
<211> LENGTH: 126
<212> TYPE: PRT
<213> ORGANISM: Mus musculus

<400> SEQUENCE: 4

```
Met Ser Ser Ala Gln Phe Leu Gly Leu Leu Leu Leu Cys Phe Gln Gly
1               5                   10                  15

Thr Arg Cys Asp Val Gln Met Thr Gln Thr Thr Ser Ser Leu Ser Ala
            20                  25                  30

Ser Leu Gly Asp Arg Val Thr Ile Asn Cys Arg Ala Ser Gln Asp Ile
        35                  40                  45

Ser Asn Tyr Leu Asn Trp Tyr Gln Gln Lys Pro Asp Gly Thr Val Lys
    50                  55                  60

Leu Leu Ile Tyr Tyr Thr Ser Arg Leu His Ser Gly Val Pro Ser Arg
65                  70                  75                  80

Phe Ser Gly Ser Gly Ser Gly Thr Asp Tyr Ser Leu Thr Ile Ser Asn
                85                  90                  95

Leu Glu Gln Glu Asp Ile Ala Thr Tyr Phe Cys Gln Gln Gly Asn Thr
            100                 105                 110

Leu Pro Trp Thr Phe Gly Gly Gly Thr Lys Leu Glu Ile Lys
        115                 120                 125
```

<210> SEQ ID NO 5
<211> LENGTH: 233
<212> TYPE: PRT
<213> ORGANISM: Artificial sequence
<220> FEATURE:
<223> OTHER INFORMATION: Mouse-human chimera

<400> SEQUENCE: 5

```
Met Glu Thr Gly Leu Arg Trp Leu Leu Leu Val Ala Val Leu Lys Gly
1               5                   10                  15

Val Gln Cys Asp Ile Gln Met Thr Gln Thr Thr Ser Ser Leu Ser Ala
            20                  25                  30

Ser Leu Gly Asp Arg Val Thr Ile Asn Cys Arg Ala Ser Gln Asp Ile
        35                  40                  45

Ser Asn Tyr Leu Asn Trp Tyr Gln Gln Lys Pro Asp Gly Thr Val Lys
    50                  55                  60

Leu Leu Ile Tyr Tyr Thr Ser Arg Leu His Ser Gly Val Pro Ser Arg
65                  70                  75                  80

Phe Ser Gly Ser Gly Ser Gly Thr Asp Tyr Ser Leu Thr Ile Ser Asn
                85                  90                  95

Leu Glu Gln Glu Asp Ile Ala Thr Tyr Phe Cys Gln Gln Gly Asn Thr
            100                 105                 110

Leu Pro Trp Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160
```

```
Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 6
<211> LENGTH: 472
<212> TYPE: PRT
<213> ORGANISM: Artificial sequence
<220> FEATURE:
<223> OTHER INFORMATION: Mouse-human chimera

<400> SEQUENCE: 6

Met Asp Thr Arg Ala Pro Thr Gln Leu Leu Gly Leu Leu Leu Leu Trp
1               5                   10                  15

Leu Pro Gly Ser Arg Cys Asp Val Gln Leu Gln Glu Ser Gly Pro Gly
            20                  25                  30

Leu Val Lys Pro Ser Gln Ser Leu Ser Leu Asn Cys Ser Val Thr Gly
        35                  40                  45

Ser Ser Ile Thr Ser Gly Tyr Tyr Trp Asn Trp Ile Arg Gln Phe Pro
    50                  55                  60

Gly Asn Lys Leu Glu Trp Met Gly Asp Ile Ser Tyr Asp Gly Ser Asn
65                  70                  75                  80

Asn Tyr Asn Pro Ser Leu Lys Asn Arg Ile Ser Ile Thr Arg Asp Thr
                85                  90                  95

Ser Lys Asn Gln Val Phe Met Lys Leu Asn Ser Val Thr Thr Glu Asp
            100                 105                 110

Thr Ala Ile Tyr Lys Cys Val Arg Glu Asp Arg Ser Gly Tyr Pro Pro
        115                 120                 125

Phe Ala Asn Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
                245                 250                 255

Pro Glu Phe Glu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285
```

Val Asp Val Ser His Glu Asp Pro Glu Val Lys Phe Asn Trp Tyr Val
            290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Ala Tyr Ala Cys Ala Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
450                 455                 460

Ser Leu Ser Leu Ser Pro Gly Lys
465                 470

<210> SEQ ID NO 7
<211> LENGTH: 120
<212> TYPE: PRT
<213> ORGANISM: Artificial sequence
<220> FEATURE:
<223> OTHER INFORMATION: Humanized sequence

<400> SEQUENCE: 7

Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Ile Thr Ser Gly
            20                  25                  30

Tyr Tyr Trp Asn Trp Ile Arg Gln Pro Pro Gly Lys Gly Leu Glu Trp
        35                  40                  45

Ile Gly Asp Ile Ser Tyr Asp Gly Ser Asn Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Val Arg Glu Asp Arg Ser Gly Tyr Pro Pro Phe Ala Asn Trp Gly Gln
            100                 105                 110

Gly Thr Leu Val Thr Val Ser Ser
        115                 120

<210> SEQ ID NO 8
<211> LENGTH: 104
<212> TYPE: PRT
<213> ORGANISM: Artificial sequence
<220> FEATURE:
<223> OTHER INFORMATION: Humanized sequence

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Trp
                85                  90                  95

Thr Phe Gly Gln Gly Thr Lys Val
            100

<210> SEQ ID NO 9
<211> LENGTH: 390
<212> TYPE: DNA
<213> ORGANISM: Artificial Sequence
<220> FEATURE:
<223> OTHER INFORMATION: Humanized sequence

<400> SEQUENCE: 9
ggatccagat gccaggtgca gctgcaggaa agcggccctg gcctggtgaa acccagccag      60
accctgagcc tgacctgcgc cgtgtacggc ggcagcatca ccagcggcta ctactggaac     120
tggatcagac agcccctgg caagggcctg gaatggatcg gcgacatcag ctacgacggc     180
agcaacaact acaaccccag cctgaagtcc agagtgacca tcagccggga caccagcaag     240
aaccagttca gcctgaagct gagcagcgtg acagccgccg acaccgccgt gtactactgc     300
gtgcgcgagg acagaagcgg ctaccccccc ttcgccaatt ggggccaggg caccctggtg     360
acagtgtcca gcgccagcac caagggcccc                                     390

<210> SEQ ID NO 10
<211> LENGTH: 324
<212> TYPE: DNA
<213> ORGANISM: Artificial sequence
<220> FEATURE:
<223> OTHER INFORMATION: Humanized sequence

<400> SEQUENCE: 10
cttaagggcg tgcagtgcga catccagatg acccagagcc ccagcagcct gagcgccagc      60
gtgggcgaca gagtgaccat cacctgtcag gccagccagg acatcagcaa ctacctgaac     120
tggtatcagc agaagcccgg caaggccccc aagctgctga tctactacac ctcccggctg     180
cacagcggcg tgcccagcag attttctggc agcggcagcg gcaccgactt caccttcacc     240
atcagcagcc tgcagcccga ggatatcgcc acctactact gccagcaggg caacaccctg     300
ccctggacct tcggccaggg tacc                                           324

<210> SEQ ID NO 11
<211> LENGTH: 98
<212> TYPE: PRT
<213> ORGANISM: Homo sapiens
<220> FEATURE:
<221> NAME/KEY: misc_feature
<222> LOCATION: (98)..(98)
<223> OTHER INFORMATION: Xaa can be any naturally occurring amino acid

<400> SEQUENCE: 11

Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Xaa

<210> SEQ ID NO 12
<211> LENGTH: 120
<212> TYPE: PRT
<213> ORGANISM: Mus musculus

<400> SEQUENCE: 12

Asp Val Gln Leu Gln Glu Ser Gly Pro Gly Leu Val Lys Pro Ser Gln
1               5                   10                  15

Ser Leu Ser Leu Asn Cys Ser Val Thr Gly Ser Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Asp Ile Ser Tyr Asp Gly Ser Asn Asn Tyr Asn Pro Ser Leu
    50                  55                  60

Lys Asn Arg Ile Ser Ile Thr Arg Asp Thr Ser Lys Asn Gln Val Phe
65                  70                  75                  80

Met Lys Leu Asn Ser Val Thr Thr Glu Asp Thr Ala Ile Tyr Lys Cys
                85                  90                  95

Val Arg Glu Asp Arg Ser Gly Tyr Pro Pro Phe Ala Asn Trp Gly Gln
            100                 105                 110

Gly Thr Leu Val Thr Val Ser Ser
        115                 120

<210> SEQ ID NO 13
<211> LENGTH: 104
<212> TYPE: PRT
<213> ORGANISM: Mus musculus

<400> SEQUENCE: 13

Asp Ile Gln Met Thr Gln Thr Thr Ser Ser Leu Ser Ala Ser Leu Gly
1               5                   10                  15

Asp Arg Val Thr Ile Asn Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

```
Thr Phe Gly Gln Gly Thr Lys Val
            100

<210> SEQ ID NO 14
<211> LENGTH: 95
<212> TYPE: PRT
<213> ORGANISM: Homo sapiens

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro
                85                  90                  95
```